United States Patent [19]

Yarrow et al.

[11] 4,203,969

[45] May 20, 1980

[54] DITHRANOL COMPOSITIONS FOR TOPICAL APPLICATIONS

[75] Inventors: Hyman Yarrow, Hitchin; Martin Whitefield, London, both of England

[73] Assignee: Drythanol Limited, London, England

[21] Appl. No.: 900,861

[22] Filed: Apr. 28, 1978

[30] Foreign Application Priority Data

Jul. 6, 1977 [GB] United Kingdom ............... 28410/77

[51] Int. Cl.² .................... A61K 31/745; A61K 31/05
[52] U.S. Cl. ..................................... 424/83; 424/346
[58] Field of Search ................................... 424/83, 346

[56] References Cited

U.S. PATENT DOCUMENTS

| | | | |
|---|---|---|---|
| 3,029,188 | 4/1962 | Cyr et al. | 424/83 |
| 3,689,667 | 9/1972 | Lee | 424/318 |

OTHER PUBLICATIONS

Remington's Pharmaceutical Sciences 13th ed., 1965, pp. 852–853.
Remington's Pharmaceutical Sciences 13th ed., 1965, pp. 1088–1089.
Chemical Abstracts 83:15595k(1975).
Chemical Abstracts 65:20655h (1966).
Dictionairre Vidal, 1978, pp. 1128–1129.
Arch. Derm. Forsch, 249, 141–152, 1974.

*Primary Examiner*—Leonard Schenkman
*Attorney, Agent, or Firm*—Stevens, Davis, Miller & Mosher

[57] ABSTRACT

Composition for topical application in the treatment of psoriasis comprises specified amounts of dithranol, an acid and anti-oxidant, petroleum jelly, which may be mixed with a spreadable synthetic rubber, water, and an emulsifier. These compositions show little tendency to spread after application to a psoriatic area and show a reduced tendency to stain.

11 Claims, No Drawings

DITHRANOL COMPOSITIONS FOR TOPICAL APPLICATIONS

THIS INVENTION relates to dithranol-containing compositions.

Dithranol (1,8,9-trihydroxyanthracene) is used in the topical treatment of psoriasis, and is one of the few effective treatments available for this condition. It suffers however from two serious disadvantages: (1) it is highly irritant to skin not affected by psoriasis and must therefore be applied with considerable care and usually under medical supervision. (2) It is easily oxidised to brown or black products and has a powerful staining effect on clothing and normal skin.

Heretofore dithranol has been dispersed as a paste in Lassars paste (white soft paraffin containing 24% of zinc oxide and 2% of salicylic acid), in yellow soft paraffin, or in Emulsifying Ointment. The salicylic acid in Lassars paste satisfactorily protects dithranol from oxidation by atmospheric oxygen for short periods but not for long term storage, due to the presence of the zinc oxide. The other formulations are even less stable. Moreover, most formulations easily spread from the psoriatic area to the surrounding skin, which then becomes very irritated and stained, and to clothing.

The present invention provides a dithranol-containing composition which spreads little or not at all after application to a psoriatic area, and which shows a greatly reduced tendency to stain clothing and bedding after application. It is moreover, relatively easy to apply even by unskilled persons.

The dithranol-containing composition of the present invention for topical application in the treatment of psoriasis comprises 0.01%, or more usually 0.05% to 1.0% of dithranol; 0.05 to 5.0%, preferably 0.1 to 1.0%, of an acid water-soluble and oil-insoluble anti-oxidant, or of a combination of a water-soluble, oil-insoluble acid and anti-oxidant; 20 to 60% of petroleum jelly (i.e. soft paraffin as in the natural Yellow Soft Paraffin or bleached White Soft Paraffin of the British Pharmacopoea), alone or mixed with a spreadable syntehtic hydrocarbon rubber, in which the dithranol is soluble; 25 to 60% of water in which the said acid-antioxidant or acid and anti-oxidant is dissolved; and 5 to 20% of an emulsifier to maintain the said petroleum jelly having the dithranol dissolved therein as a stable emulsion in the water having the acid-antioxidant or acid and anti-oxidant dissolved therein; the said percentages being by weight based on the total weight of the composition.

Although dithranol exerts its optimum therapeutic effect in alkaline or neutral media, it rapidly deteriorates under thes conditions because of atmospheric oxidation, and therefore the aqueous, continuous phase in the compositions of the present invention is maintained in the acid state by inclusion of a water-soluble acid. The acid must, of course, by physiologically harmless and must remain substantially entirely in the aqueous phase in the composition. Citric acid is a suitable acid. The anti-oxidant should also be water soluble and may be separate from the acid. It is preferred, however, to use a compound which is water-soluble and oil-insoluble (i.e. insoluble in the petroleum jelly) and is both an acid and an anti-oxidant. Ascorbic acid and sodium metabisulphite are examples of such compounds, and the use of ascorbic acid is preferred. The combination of maintaining the aqueous phase in an acid condition and also including an anti-oxidant in the composition leads to a high degree of stabilisation of the dithranol. Moreover, since the acid is substantially insoluble in the petroleum jelly in which the dithranol is dissolved, after the composition has been applied to the psoriatic area and the water has evaporated, the acid becomes effectively separated from the dithranol and does not interfere with the therapeutic effect of the latter, which is no longer in an acid environment.

As already indicated, the dithranol must be substantially completely dissolved in the petroleum jelly. While it is possible to use compositions in which part of the dithranol is not dissolved in the petroleum jelly, such undissolved dithranol is able to act only slowly on the psoriatic areas, and the effectiveness of a composition containing undissolved dithranol is substantially the same as that of a similar composition containing only sufficient dithranol to saturate the petroleum jelly. If it is desired to include in white or yellow soft paraffin BP a concentration of dithranol greater than 0.25%, the solubility of the dithranol in the oily phase may be increased by adding to the latter a proportion, usually up to 25% based on the total weight of the composition, of a spreadable synthetic hydrocarbon rubber, preferably a polybutene having a molecular weight from 2000 to 3000, e.g. a polybutene having a molecular weight of about 2450 and a kinematic viscosity of 195000 cSt at 37.8° C., in order to produce a mixture in which the dithranol is completely dissolved. Moreover, the addition of such a material to the composition not only restricts flow of the composition on the skin but after rubbing in leaves a tacky surface which is non-mobile and can be covered with a layer of talc to form a dry film and so prevent soiling of bedding and clothing.

The emulsifier serves to maintain the petroleum jelly or mixture containing the same having the dithranol dissolved therein, as a discontinuous phase in the acid aqueous phase. Suitable emulsifiers, which must, of course, be stable in the presence of dithranol and acid and be physiologically harmless, are available commercially. Suitably, an emulsifier which consists of a mixture of a long-chain fatty alcohol and a non-ionic surfactant in proportions from 70:30 to 90:10 by weight may be used. Suitable commercially available material are cetomacrogol 1000, which contains 80% cetostearyl alcohol and 20% polyethylene glycol-1000 monocetyl ether, and lanbritol wax N21.

It is usually desirable to include a preservative in the composition, for example, chlorocresol in a concentration of 0.05 to 0.2% by weight.

The composition may be made by conventional techniques. Thus, the dithranol may be mixed with the white soft paraffin or other petroleum jelly and the polybutene (if used) and dissolved therein. The ascorbic acid or other acid is dissolved in the water which has been boiled to remove oxygen. The two are then mixed in the presence of the emulsifier and the whole is milled to produce a stable emulsion.

The compositions of the invention are easily spreadable because of the water which they contain. They may be divided into two kinds: (1) Compositions in which a polybutene is incorporated as described above where after application the water evaporates or is absorbed together with some of the petroleum jelly leaving behind a viscous tacky film of the polybutene which may be covered with talc to produce a dry non-staining film which prevents soiling of clothing and bedding. This type of composition is particularly useful where higher concentrations of dithranol are used. (2) Compositions not containing polybutene which can be rubbed onto the skin as a vanishing cream leaving little or no surface film, thus avoiding staining of clothing and bedding. The latter type of composition may contain very low concentrations of dithranol, i.e. 0.01 to 0.05% by weight; such low concentrations have been found to be effective if use of the compositions is sufficiently prolonged, and they have the advantage that they reduce still further the possibility of harmful effects if the compositions are misused. The compositions are easy to apply and leave no greasiness on the skin surface.

The following are preferred formulations in accordance with the present invention:

EXAMPLE 1

The following ingredients are mixed together in the manner already described:

| | |
|---|---|
| Dithranol | 0.5% |
| Ascorbic Acid | 0.5% |
| White Soft paraffin BP | 25% |
| Hyvis 200 (a polybutene having a viscosity of 195000 cSt at 37.8° C.) | 25% |
| Lanbritol wax | 10% |
| Chlorocresol | 0.1% |
| Water | 39.0% |

EXAMPLE 2

| | |
|---|---|
| Dithranol | 0.25% |
| Ascorbic Acid | 0.5% |
| White Soft paraffin BP | 50% |
| Lanbritol wax | 10% |
| Chlorocresol | 0.1% |
| Water | 39.2% |

This latter composition, which contains no polybutene, and a relatively low concentration of dithranol, is more suitable than the composition of Example 1 for application to the scalp and other areas where a relatively low concentration of dithranol and the absence of polybutene (which causes hair to tangle) are desirable.

The compositions of the invention are used in the same way as prior known compositions containing dithranol and have the advantages over the latter already mentioned. Thus they may be applied to the psoratic area by hand two or more times a day. No especial care is needed for this application as the risks of irritation of surrounding skin and staining are substantially reduced by the new compositions. Treatment is continued until the psoriasis is cured. No particular problems are caused by prolonged treatment if such proves necessary and in this connection it is a major advantage that the new compositions can be applied by the patient himself and do not require application by a doctor or nurse.

We claim:

1. A composition for topical application comprising:
   0.01 to 1% of dithranol;
   0.05 to 5% of a water-soluble, oil-insoluble acid antioxidant or of a combination of a water-soluble, oil-insoluble acid and a water-soluble, oil-insoluble antioxidant;
   20 to 60% of petroleum jelly, along or mixed with a spreadable synthetic hydrocarbon rubber, in which dithranol is soluble;
   25 to 60% of water in which the said acid-antioxidant or combination of acid and antioxidant is dissolved; and
   5 to 20% of an emulsifier to maintain as a stable emulsion the said petroleum jelly, alone or mixed with a spreadable synthetic hydrocarbon rubber, as a discontinuous oil phase dispersed in a continuous aqueous phase;
   the said precentages being by weight based on the total weight of the composition;
   the dithranol being substantially completely retained in the discontinuous oil phase, and the acid-antioxidant or combination of acid and antioxidant being dissolved in and substantially completely retained in the continuous aqueous phase,
   whereby when in said composition the dithranol is protected from oxidation during storage but when the composition is applied to the skin the water in said aqueous phase evaporates or is absorbed by the skin and the dithranol is made available.

2. A composition according to claim 1 containing 0.05 to 1.0% of dithranol.

3. A composition according to claim 2 containing 0.1 to 1% of the acid-antioxidant or of the combination of acid and antioxidant.

4. A composition according to claim 2 containing a water-soluble, oil-insoluble acid-antioxidant.

5. A composition according to claim 2 wherein the water-soluble, oil-insoluble acid antioxidant is ascorbic acid.

6. A composition according to claim 2 in which the petroleum jelly is mixed with a polybutene having a molecular weight of 2000 to 3000.

7. A composition according to claim 2 in which the emulsifier is a mixture of a long-chain fatty alcohol and a non-ionic surfactant.

8. A composition according to claim 2 which also includes a preservative in a concentration of 0.05 to 0.2% by weight.

9. A composition according to claim 1 comprising:
   0.05 to 1.0% of dithranol;
   0.1 to 1% of ascorbic acid;
   20 to 60% of petroleum jelly alone or mixed with a polybutene having a molecular weight of 2000 to 3000;
   25 to 60% of water;
   5 to 20% of a mixture of a long-chain fatty alcohol and a non-ionic surfactant; and
   0.05 to 0.2% by weight of a preservative;
   the said percentages being by weight based on the total weight of the composition.

10. A composition according to claim 1 wherein said emulsifier is a nonionic surfactant.

11. A method of treating psoriasis which comprises applying to a psoriatic area an effective amount of a composition as defined in claim 1.

* * * * *